(12) United States Patent
Dull et al.

(10) Patent No.: US 8,844,450 B2
(45) Date of Patent: Sep. 30, 2014

(54) SYSTEMS, COMPONENTS AND METHODS FOR DELIVERING LIQUID SUBSTANCES

(75) Inventors: Lawrence Clifford Dull, Greensboro, NC (US); Walter Theodore Meisner, III, Greensboro, NC (US); Joshua Jenkins, Greensboro, NC (US); Dustin Mack, Greensboro, NC (US)

(73) Assignee: Syngenta Crop Protection LLC, Greensboro, NC (US)

( * ) Notice: Subject to any disclaimer, the term of this patent is extended or adjusted under 35 U.S.C. 154(b) by 1357 days.

(21) Appl. No.: 12/599,728

(22) PCT Filed: Nov. 16, 2007

(86) PCT No.: PCT/US2007/084899
§ 371 (c)(1),
(2), (4) Date: Jun. 2, 2011

(87) PCT Pub. No.: WO2008/140575
PCT Pub. Date: Nov. 20, 2008

(65) Prior Publication Data
US 2014/0083340 A1    Mar. 27, 2014

Related U.S. Application Data

(60) Provisional application No. 60/917,360, filed on May 11, 2007.

(30) Foreign Application Priority Data

Nov. 16, 2007    (WO) ................. PCT/US2007/084899

(51) Int. Cl.
| | |
|---|---|
| A01B 49/04 | (2006.01) |
| A01N 25/00 | (2006.01) |
| A01C 23/00 | (2006.01) |
| A01B 49/06 | (2006.01) |
| A01C 23/04 | (2006.01) |
| A01M 7/00 | (2006.01) |

(52) U.S. Cl.
CPC .............. *A01N 25/00* (2013.01); *A01C 23/008* (2013.01); *A01B 49/06* (2013.01); *A01C 23/047* (2013.01); *A01M 7/0085* (2013.01); *Y10S 111/90* (2013.01)
USPC ........... 111/120; 111/127; 111/130; 111/900; 141/114; 229/117.27; 383/56; 239/1; 239/10

(58) Field of Classification Search
CPC .... A01B 49/06; A01C 23/008; A01C 23/047; A01N 25/00; A01M 7/0085
USPC ......... 111/120, 900, 127, 130, 186–188, 170, 111/14; 53/133.1, 133.2, 136.4, 434; 141/114; 229/103.3, 117.3, 117.35, 229/117.27; 383/42, 56; 239/1, 10
See application file for complete search history.

(56) References Cited

U.S. PATENT DOCUMENTS

| | | |
|---|---|---|
| 2,367,717 A | 1/1945 | Davidson |
| 3,147,904 A | 9/1964 | Larson |

(Continued)

OTHER PUBLICATIONS

Landers, Andrew Dr.: "The Theory and Constituent Parts of a Direct Injection Sprayer", Quarbarton, Sopworth, Nr Chippenham, Wilts. SN14 6PT, New York.

(Continued)

*Primary Examiner* — Christopher J Novosad
(74) *Attorney, Agent, or Firm* — R. Kody Jones (57) ABSTRACT

A product reservoir is provided that includes a flexible bag and a carton to receive and retain the flexible bag. The bag may contain liquid chemical substances that are dispensed from the bag through a bag spout. The product reservoir may serve as a component to a fluid delivery system, such as a direct injection system employed by agricultural seed planting machines. When the bag is connected to the direct injection system, the liquid substance is placed in fluid communication with a delivery device whereby the substance can be dispensed to a selected area for treatment. The liquid substance may be mixed in-line with water received from a water reservoir prior to being dispensed by the delivery device. The planting machine may be equipped with a plurality of product reservoirs. A method of applying a liquid pesticide to a selected area is also provided.

31 Claims, 9 Drawing Sheets

(56) References Cited

U.S. PATENT DOCUMENTS

| | | |
|---|---|---|
| 3,463,859 A | 8/1969 | Covey et al. |
| 4,171,710 A | 10/1979 | Boynton et al. |
| 4,771,939 A | 9/1988 | Wilkins |
| 4,815,631 A | 3/1989 | Eeg et al. |
| 4,826,083 A | 5/1989 | Vanderjagt |
| 4,913,316 A | 4/1990 | Richter |
| 5,016,817 A | 5/1991 | Ghate et al. |
| 5,074,429 A | 12/1991 | Konkel et al. |
| 5,222,324 A | 6/1993 | O'Neall et al. |
| 5,314,088 A | 5/1994 | Heuberger et al. |
| 5,494,074 A | 2/1996 | Ramacier, Jr. et al. |
| 5,749,493 A | 5/1998 | Boone et al. |
| 5,915,596 A | 6/1999 | Credle, Jr. |
| 5,931,882 A | 8/1999 | Fick et al. |
| 5,938,109 A | 8/1999 | Sainz et al. |
| 6,223,981 B1 | 5/2001 | Gunder |
| 6,289,829 B1 | 9/2001 | Fish et al. |
| 6,607,097 B2 | 8/2003 | Savage et al. |
| 6,827,237 B2 | 12/2004 | Yorn et al. |
| 7,007,825 B2 | 3/2006 | Crosland et al. |
| 7,152,541 B2 | 12/2006 | Ptacek |
| 2003/0201280 A1 | 10/2003 | Geshay |
| 2006/0071021 A1 | 4/2006 | Steeves et al. |

OTHER PUBLICATIONS

Landers, Andrew et al.: Engineer Control Technology Study "Survey of Engineering Control Technology for Pesticide Application", Jan. 1-Dec. 31, 2000, Cornell University, Ithaca, New York, pp. 7-26.

SYSTEMS, COMPONENTS AND METHODS FOR DELIVERING LIQUID SUBSTANCES

This application is a 371 of International Application No. PCT/US2007/084,899 filed Nov. 16, 2007, which claims priority to U.S. Application No. 60/917,360 filed May 11, 2007, the contents of which are incorporated herein by reference.

BACKGROUND

The present disclosure broadly relates to a fluid delivery system and components associated therewith. The present disclosure is more particularly directed to systems, components and methodologies for the application of liquid chemical substances, such as pesticides, to a selected area to be treated.

Farming has evolved significantly over time enabling farmers to increase crop yield and optimizing both time and agricultural land. Centuries ago, farming was very labor intensive and families typically lived on small farms using domesticated animals and simple tools to prepare the land and plant crops. The long hours in the field during these times generally resulted in low product yields. Over time, horse powered farming equipment was replaced by steam powered tractors and ultimately by gasoline and diesel powered tractors.

Today, farming can be described as an integrated system of specialized equipment, science, and computers. The marriage of farming, technology, and science has particularly enhanced crop sustainability and improved efficiency and profitability. Indeed, the advent of synthetic chemicals has successfully increased crop yields and it is estimated that approximately 2.5 million tons of pesticides are currently used each year.

The agricultural industry, as a whole, strives to improve its agricultural products, farming methodologies, and equipment not only to optimize crop yield, but to achieve a suitable balance among a number of variables such as the social, environmental, and economic aspects of farming in general. This balance can, arguably, be best achieved through the input and interaction of all stakeholders, including the growers, researchers, manufacturers, policy makers, farm workers, distributors, retailers and consumers.

One component of this industry that is realizing its role in creating this balance is the agrochemical industry. While it is important for agrochemical companies to continue to improve pesticide formulations, it is equally important for these companies to recognize that the packaging, transportation, storage, use, and ultimate disposal of their products and product containers should also be taken into consideration. Companies that strive not to just sell their chemical products, but also facilitate the use and handling of the product throughout its lifecycle can add value not only to their retailers, distributors, and growers, but also provide a spectrum of environmental, financial, and social benefits.

To this end, some agrochemical companies have developed and implemented strategies and programs that reduce the impact of their products on the environment. For example, some companies have made substantial advancements in improving the integrity of their product packaging and promoting reusable packaging and recycling programs to systematically and efficiently refill the containers as incentives to use these programs. The advancements made thus far in packaging solutions and efforts to employ reusable containers appear to be alleviating the environmental impact of agrochemical products and other hazardous materials. Some benefits realized, for example, include conservation of materials, conservation of landfill space, and improved soil and water quality.

Another area in which some agrochemical companies are investing resources is the development of innovative ways to facilitate and promote precision farming and operator safety. Precision farming generally involves the gathering of information, and the subsequent analysis of that information to then employ the appropriate technology to optimize crop yield. Precision farming oftentimes incorporates a variety of modern technological tools including global positioning system, mapping software, yield monitors, variable rate technology, and remote sensing equipment. Farm equipment such as crop sprayers that incorporate this technology has been developed. Specifically, crop sprayers equipped with direct injection systems are currently assisting farmers in utilizing precision farming techniques while reducing exposure to pesticides by those who operate the equipment.

Crop sprayers equipped with direct injection systems usually include a source of a liquid chemical product, such as a pesticide and a separate source of water. A metered flow of the pesticide is then injected into a water stream where the pesticide is diluted to a specified concentration prior to being sprayed to the area to be treated. The injection pumps can be switched on and off as required to spray specified areas and the amount of pesticide to be applied can be adjusted depending upon the level of pest infestation. Since the pesticide and the water remain separate, the direct injection system eliminates the need for a mixing tank, which is common to many crop sprayers in use today. Furthermore, some direct injection systems are adapted to be "closed transfer systems", which means that the operator does not physically transfer the pesticide from its original container to a mixing tank or other tank on the crop sprayer. Crop sprayers incorporating this technology are showing increasing promise for replacing more conventional crop sprayers.

Although the aforementioned improved packaging solutions, recycling efforts, and development of precision farming technology generate noticeable environmental, health, and economic benefits, there continues to be a need to develop improved technology to optimize these benefits. Moreover, as precision farming technology evolves and begins to replace conventional farming technology, there is a need for agrochemical companies to develop improved packaging solutions that safeguard the health and safety of those operating the equipment, while facilitating the use of the equipment. The present invention is directed to meeting these needs.

SUMMARY OF THE INVENTION

According to the present disclosure, a product reservoir is provided that is adapted to contain a product to be dispensed to a selected area. The product reservoir broadly includes a flexible bag and a carton. The bag has a bag interior for containing the product and a spout in communication with the bag interior. The carton has a sidewall extending around a carton interior that is sized and adapted to receive and retain the flexible bag and has opposing first and second ends.

The carton sidewall is constructed of a plurality of panels including a front panel and a back panel in parallel and spaced relation to the front panel. A pair of opposing side panels extend between the front and back panels. The carton has a carton interior with opposing first and second open ends. The carton is further provided with first and second end closures adapted to cover the first and second open ends and enclose the carton interior when in a closed state. The first and second ends are formed from a plurality of flaps. The first end closure includes a first front flap, a first back flap, and a pair of first side flaps, while the second end closure includes a second front flap, a second back flap, and a pair of second side flaps. The carton may also be provided with a removable spout access panel that extends continuously between a portion of the first front flap and a portion of the front panel. Removal of the access panel reveals or thereby forms an opening sized and adapted to permit access to the spout and allow at least a portion of the spout to extend therethrough.

The carton side panels may have a length that is greater than the length of both the front and back panels such that the carton is generally rectangular in configuration and formed of a corrugated material. The sidewall panels, the first and second closure flaps, and the spout access panel may all be formed as an integral, one-piece construction of corrugated material.

The spout access panel is preferably accessible when the first and second closure flaps are in the closed state. To this end, a pair of side closure flaps may be adhered to the front and back panels, and may further be provided with respective edge portions that are in spaced relation to one another thereby to form a gap to permit access to the panel. The remaining portions of each respective flap edge are preferably in confronting relation to one another.

Access panel may further be formed by a series of perforations. The perforations are formed in the first front flap and the front panel with sufficient depth to be easily punched out or removed to form or thereby expose the spout opening. The opening may be described has having two portions—a first portion formed in the first front flap and a second portion formed in the front panel. The second portion of the opening may be generally U-shaped in configuration and sized and adapted to nestably receive at least a portion of the spout therethrough.

With respect to the bag, it may be filled via the spout with a selected liquid such as an agricultural chemical. The bag may include a bag wall surrounding the bag interior that may be formed of a polyethylene. More particularly, the bag wall may be formed of a top panel and a bottom panel joined about their respective peripheries thereof. Both the top and bottom panels may be constructed of three sheets of polymer film.

The present disclosure also contemplates a fluid delivery system, wherein the product reservoir generally described above is incorporated as a component thereof. As such, the spout is adapted to be connected to a fluid pathway, which permits the bag interior to be in fluid communication with a delivery device such as a delivery tube, nozzle, or other device commonly known in the art. This interconnection may be formed by a coupler, which couples a conduit to the spout. A water reservoir may also be provided that is in fluid communication with the selected delivery device.

More particularly, the product reservoir may be interconnected with a direct injection system whereby liquid chemical treatment and water are drawn from their respective reservoirs, mixed in-line, and applied via the deliver device. As such, the present disclosure contemplates both an improvement to a conventional direct injection system, as well as agricultural equipment incorporating the same, whereby the chemical treatment is applied in a closed transfer system. A plurality of product reservoirs can be connected to the direct injection system via an array of conduits or fluid pathways. In this way, a sufficient volume of liquid chemical treatment may be available for large-scale treatment operations. For example, eight product reservoirs, each containing approximately 2.5 gallons of liquid chemical treatment can be supported by an agricultural seed planting machine thereby to accomplish an in-furrow application of a selected agricultural product.

The present disclosure also contemplates a method of applying a liquid pesticide wherein a product reservoir, such as described above, is provided. The method includes drawing the liquid chemical treatment from the flexible bag and directing the treatment to a delivery device, which applies the treatment to the selected area. The method may further include the steps of removing the spout access panel, extending at least a portion of the spout through the spout opening, and attaching a coupler thereto. The coupler is operative to place the bag in fluid communication with a delivery device, which forms a component of a direct injection system. The method may be used to accomplish in furrow application of a liquid pesticide wherein a plurality of product reservoirs are supported by a planting assembly operative to form a seed furrow and deposit both seeds and liquid chemical treatment prior to closing the furrow.

DETAILED DESCRIPTION OF THE EXEMPLARY EMBODIMENTS

The exemplary embodiments described herein broadly concerns fluid delivery systems and components therefore. The fluid delivery system and its components have particular utility for the application of liquid chemical substances, such as liquid pesticides, fertilizers, and other treatments to a selected area to be treated. As used herein, the term "pesticides" broadly encompasses a variety of formulations tailored to prevent, destroy, repel, or lessen the damage of a particular pest. There are several general categories of pesticides, including herbicides, insecticides, fungicides, and rodenticides, to name a few.

The present disclosure more particularly relates to a system for delivering liquid pesticide products contained in a pesticide reservoir that generally includes a flexible packaging housed within a container or carton, such as a box formed of corrugated material. The pesticide reservoir is adapted to connect to a direct injection system operative to inject the pesticide from the flexible packaging and into a water stream prior to be sprayed through a plurality of nozzles. The present invention is also directed to a method of applying liquid agrochemical products.

Figure 1:
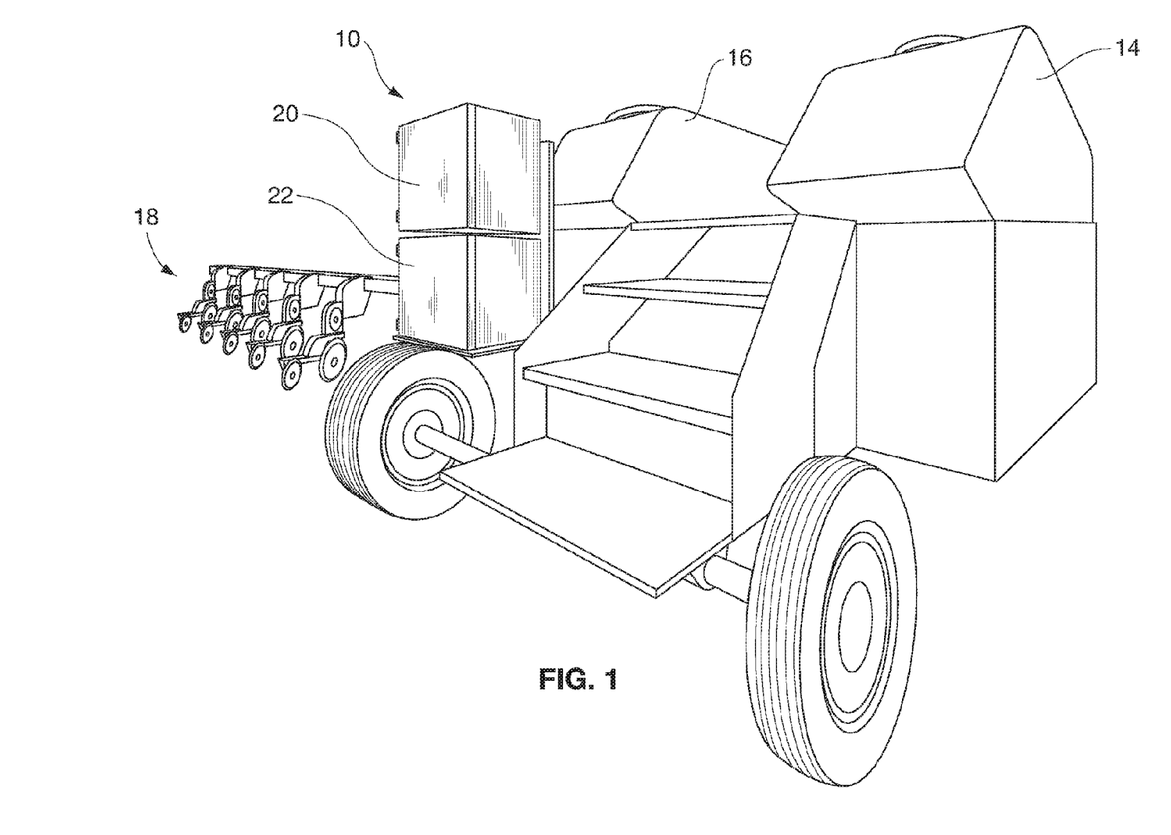
FIG. 1 is a perspective view of a product application system incorporating two cabinets containing product reservoirs according to the present invention.

To better understand this fluid delivery system and its utility, reference is first made to FIG. 1, which shows a portion of product application system 10, which is operative to both deposit seeds and deliver pesticides. Product application system 10 is shown here in the form of a multi-row planter that is adapted to connect to and be pulled by a tractor (not shown). Product application system 10 shown here generally includes seed reservoir 14, water reservoir 16, and a plurality of spaced apart row units 18. Additional reservoirs and planting equipment may also be components of this system, however, and the ones shown here are for illustrative purposes.

Each row unit 18 may be constructed, for example, as described in U.S. Pat. No. 6,289,829 B1, issued on Sep. 18, 2001 to Fish et al. and assigned to Aventis CropSceince S.A. (the "'829 patent"), the contents of which are incorporated herein by reference. As shown in FIG. 1 and as described in the '829 patent, each row unit 18 is operative to form a seed furrow. Seeds received from a seed source, such as seed reservoir 14, may be singulated by a conventional seed meter and deposited into the furrow via a seed tube, or other device known in the art. In addition to depositing the seeds, row units 18 also include a delivery tube, nozzle, or other appropriate conventional device that administers a liquid chemical treatment into the furrow. Depending upon the structure of the row unit, this treatment can be applied prior to the seed being deposited in the furrow, or directly over the top of the seed and therearound after the seed is deposited. As product application system 10 continues to move in a forwardly direction, the closing wheels close the soil over the seeds. This particular treatment method is commonly referred to as "in-furrow treatment" and as should be appreciated by one of ordinary skill in the art, any suitable liquid chemical treatments can be applied this way such as liquid fertilizers, pesticides, or agricultural additives, to name a few.

As generally described above, the product application system 10 is associated with a fluid delivery system, which is operative to transfer the liquid chemical treatment from a source to a delivery device such as a tube or nozzle. This fluid delivery system can be described as a direct injection system, as known in the art. Direct injection systems are operative to draw water from a water reservoir thereby to form a water stream and liquid chemical treatment from a separate product reservoir. The chemical treatment is injected into the water stream and mixed in a mixing chamber or other inline device at a location upstream from the delivery device. The mixture thereby formed is then dispensed via the delivery device into the furrow.

One such liquid chemical treatment that can be applied in this way is an insecticide such as Force® CS, which is a product provided by Syngenta Crop Protection, Inc., located in Greensboro, N.C., and the assignee to this application. The Force® CS product is a pre-emergence insecticide that when applied to seeds as a seed treatment, assists in the control of soil pests that can damage or otherwise destroy germinating seedlings.

Figure 2:
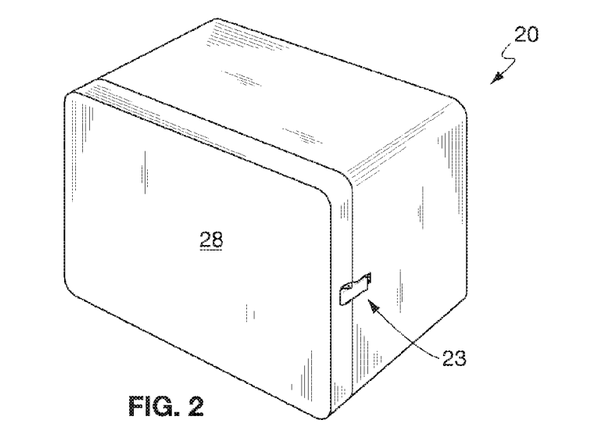
FIG. 2 is a perspective view of a representative cabinet shown in FIG. 1.
Figure 3:
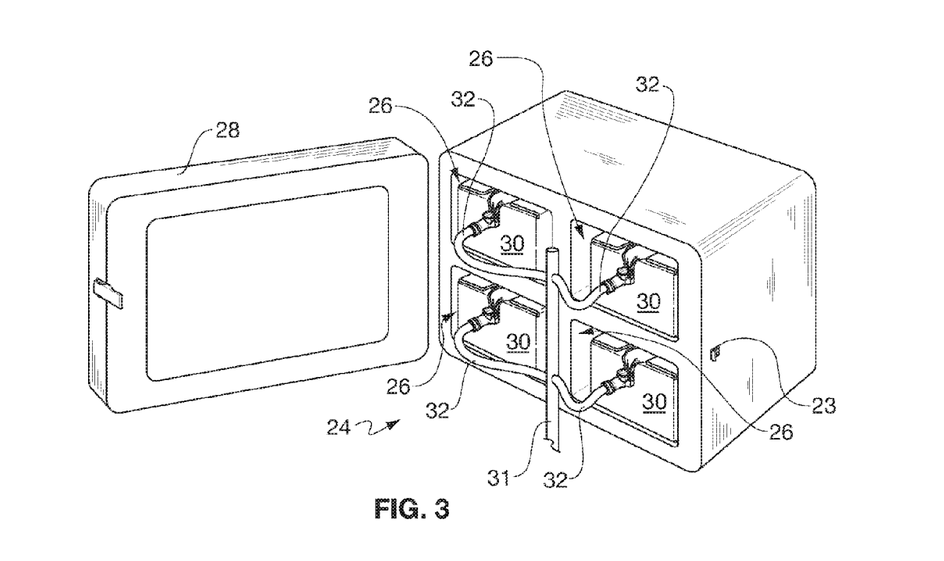
FIG. 3 is a perspective view of the cabinet shown with the cabinet door open to reveal the four (4) product reservoirs contained therein.

With the above description in mind, then, the components of the fluid delivery system can be described in more detail. With continued reference to FIG. 1 and additional reference to FIGS. 2 and 3, product application system 10 includes a plurality of product reservoirs 30, which are housed in cabinets 20 and 22. Since cabinets 20 and 22 are identical in structure, a representative cabinet 20 will be discussed in more detail. As best shown in FIG. 3, cabinet 20 has an interior 24 that is divided into four bays 26. Each bay 26 is sized and adapted to receive a single product reservoir 30 therein. Cabinet 20 includes door 28 associated therewith that when open, permits access to the interior 24 as shown in FIG. 3. Door 28 can be closed to conceal the interior, as shown in FIG. 2 and a conventional latching device 23 can be used to keep the door closed. With continued reference to FIG. 3, product reservoirs 30 are associated with an array of fluid pathways shown here in the form of conduits 31 and 32, which are adapted to interconnect product reservoirs 30 to the direct injection system. As shown, each product reservoir is directly connected to conduit 32, which is connected to or otherwise feeds into one central conduit 31. Central conduit line 31 extends underneath cabinet 20 and is adapted to connect to the direct injection system thereby placing each product reservoir 30 in fluid communication with both the in-line mixing chamber and delivery device. As should be appreciated, the direct injection system will also receive a separate, central conduit line in a similar manner from cabinet 22.

Figure 4:
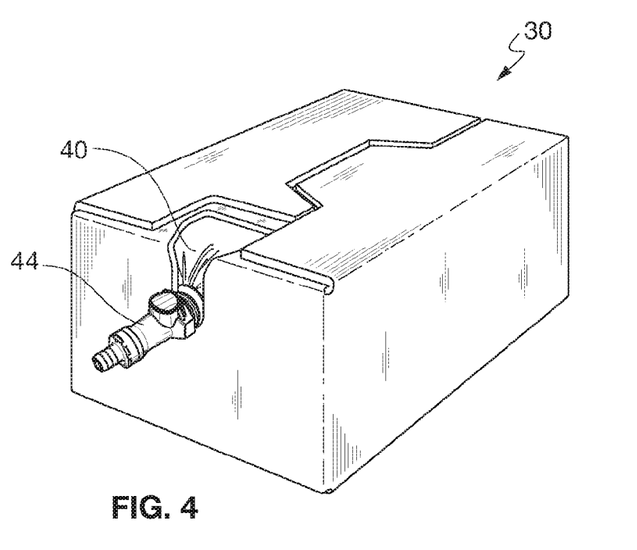
FIG. 4 is a perspective view of a representative product reservoir shown in FIG. 3 and the coupling assembly that couples the product reservoir to the direct injection system.
Figure 5:
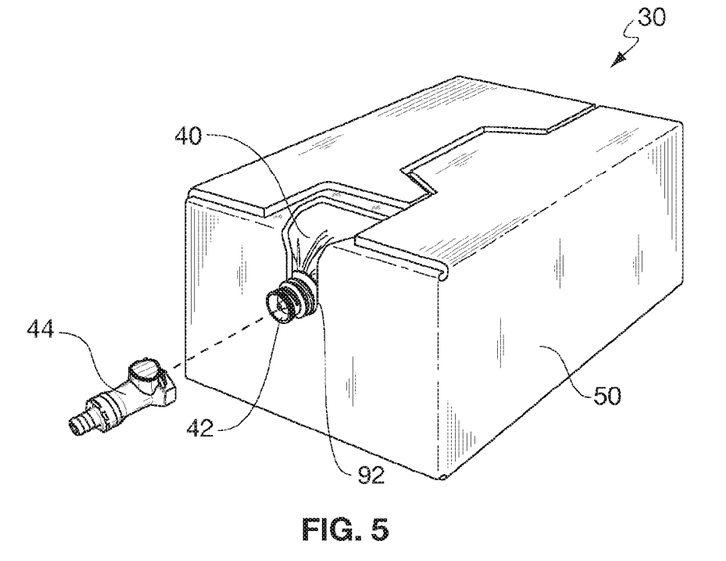
FIG. 5 is an exploded perspective view of the product reservoir and coupling assembly.
Figure 6:
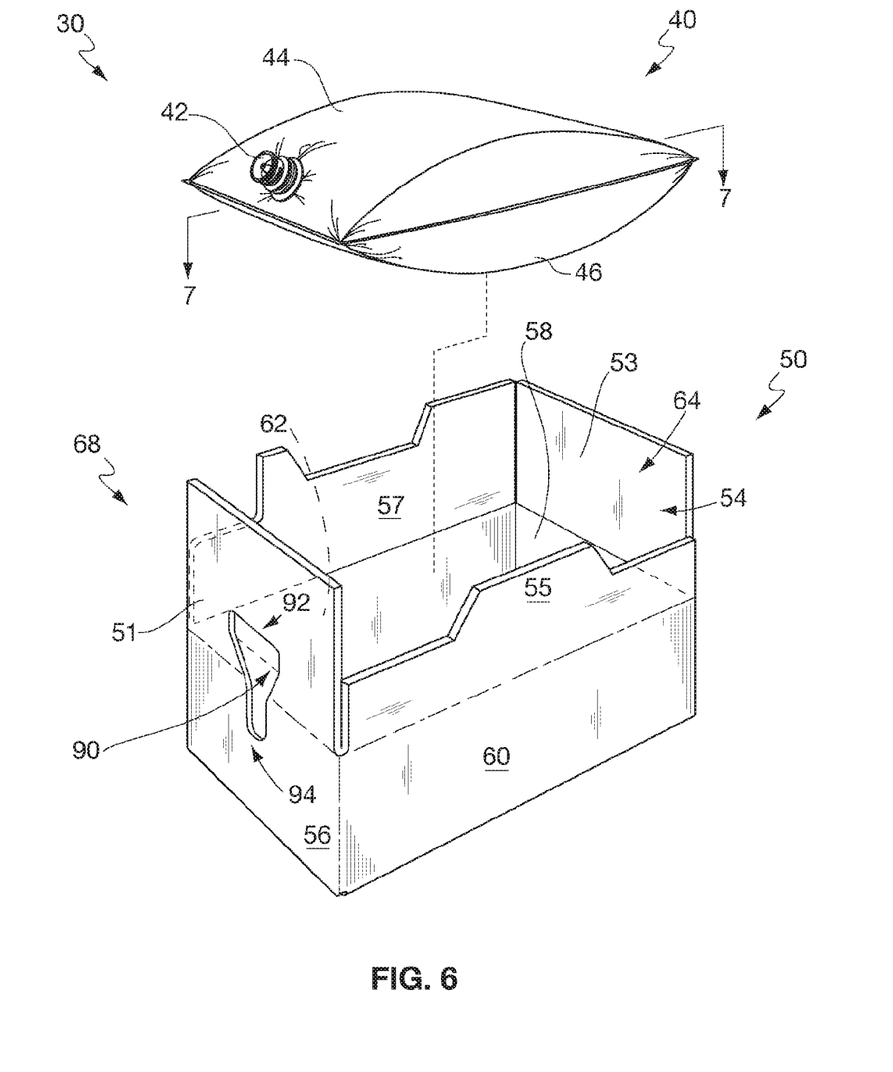
FIG. 6 is an exploded perspective view of the carton and flexible packaging components of the product reservoir.

A representative one of product reservoirs 30 is shown in FIGS. 4-6. Product reservoir 30 generally includes a collapsible container shown here in the form of flexible bag 40, received in carton 50. Flexible bag 40 has a bag interior adapted to receive and contain the liquid chemical product and a bag fitment in the form of spout 42 that communicates with the bag interior. Spout 42 may be provided with a removable seal that covers the opening prior to use. For example, a removable foil covering, such as known in the art, may be used to seal the spout opening as well as to provide tamper evidence. Other suitable tamper evidence seals are also contemplated.

Once the seal is removed, coupler 44 can be used to couple spout 42 with a conduit, such as conduit 32, to ultimately place the bag interior in fluid communication with the direct injection system. Coupler 44 may be, for example, a quick connection valve assembly, such as currently provided by Colder Products Company, located in St. Paul, Minn. ("CPC"). The features of the quick connection valve assembly generally include two components—a male coupling member and a female coupling member, as more fully described, for example, in U.S. Pat. No. 5,494,074 issued on Feb. 27, 1996 to Ramacier, Jr., et al. and assigned to CPC, the contents of which are incorporated herein by reference. The male coupling member is adapted to connect directly with the bag spout while the female coupling member connects to the male coupling and the direct injection system.

Flexible bag 40 should be constructed of a suitable material or plurality of materials sufficient to contain hazardous substances when employed with a planter system as described. For example, with reference to FIGS. 6 and 7, flexible bag 40 may have a bag wall constructed of a top panel 44 and bottom panel 46 that are joined together about their respective peripheries, such as by heat sealing, suitable adhesive, or other conventional method. Panels 44 and 46 may each be formed from three sheets of flexible material, inner sheet 43, middle sheet 45, and outer sheet 47, each of which are bonded to each other about their respective peripheries.

Figure 7:
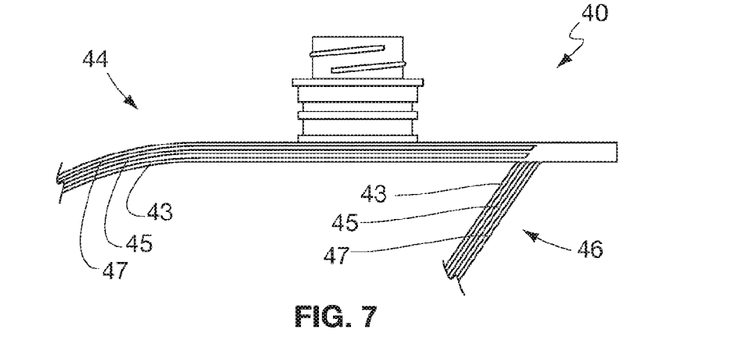
FIG. 7 is a cross-sectional view of the flexible packaging taken about lines 7-7 in FIG. 6.

Inner sheet 43 may be, for example, a single layer, low density polyethylene, non-barrier film such as the film marketed by Scholle Corporation of Irvine, Calif. (Scholle) under the name FlexiTech38. Outer sheet 47 may be a non-barrier film that provides strong seals, bag toughness, and flex crack resistance. More particularly, outer sheet 47 may be formed of a combination of polyethylene and biaxially oriented nylon material, such as Scholle's DuraTech46HF. Middle sheet 45 may act as a barrier between sheets 43 and 47, and be constructed from polyethylene, ethylene vinyl alcohol, nylon, including biaxially oriented nylon, metalized polymer, foil or a combination of these materials. In addition, if desired, nanocomposites could be incorporated into the material. Examples of a suitable middle sheet 45 are Scholle's Metalized DuraShield45, Clearshield46, or Hybar45HF.

As should be appreciated, other suitable flexible bag constructions are contemplated. For example, top and bottom panels 46 and 47 may be constructed of two sheets, four sheets, or any number of sheets or material suitable for containing liquid chemical treatments. With respect to a two sheet construction, top and bottom panels 44 and 46 could be constructed with a first sheet as described above with respect to inner sheet 43, and a second sheet as described above with respect to middle sheet 45. Alternatively, the top and bottom panels could include a middle and an outer sheet formed of the same material and an inner sheet formed of a different material.

Additionally, the size of flexible bag 40 may also vary. For example, for uses with a system such as the direct injection system, flexible bags 40 may be constructed to contain between approximately one (1) and five (5) gallons of chemical product, and may specifically hold approximately two and a half (2.5) gallons. As contemplated, the product reservoir described herein may also be used with a pumping system other than the direct injection system, such as a hand pump. As such, flexible bag 40 may be constructed to contain between approximately 250 mL and one gallon.

In addition, bag 40 may further be provided with a flexible conduit, such as pair of ribs or a web strip, as more fully described in U.S. Pat. No. 5,749,493 issued on May 12, 1988 to Boone et al., U.S. Pat. No. 5,941,421 issued on Aug. 24, 1999 to Overman et al., and U.S. Pat. No. 6,102,252 issued on Aug. 15, 2000 to Overman et al., each assigned to The Coca-Cola Company, located in Atlanta, Ga. (Coca-Cola) and incorporated herein by reference. As described in the Coca-Cola patents referenced herein, the protrusions or ribs form a conduit which cannot be closed off by the atmospheric pressure on the walls of the bag. As such, the bag interior should remain in communication with the spout during operation.

Figure 8:
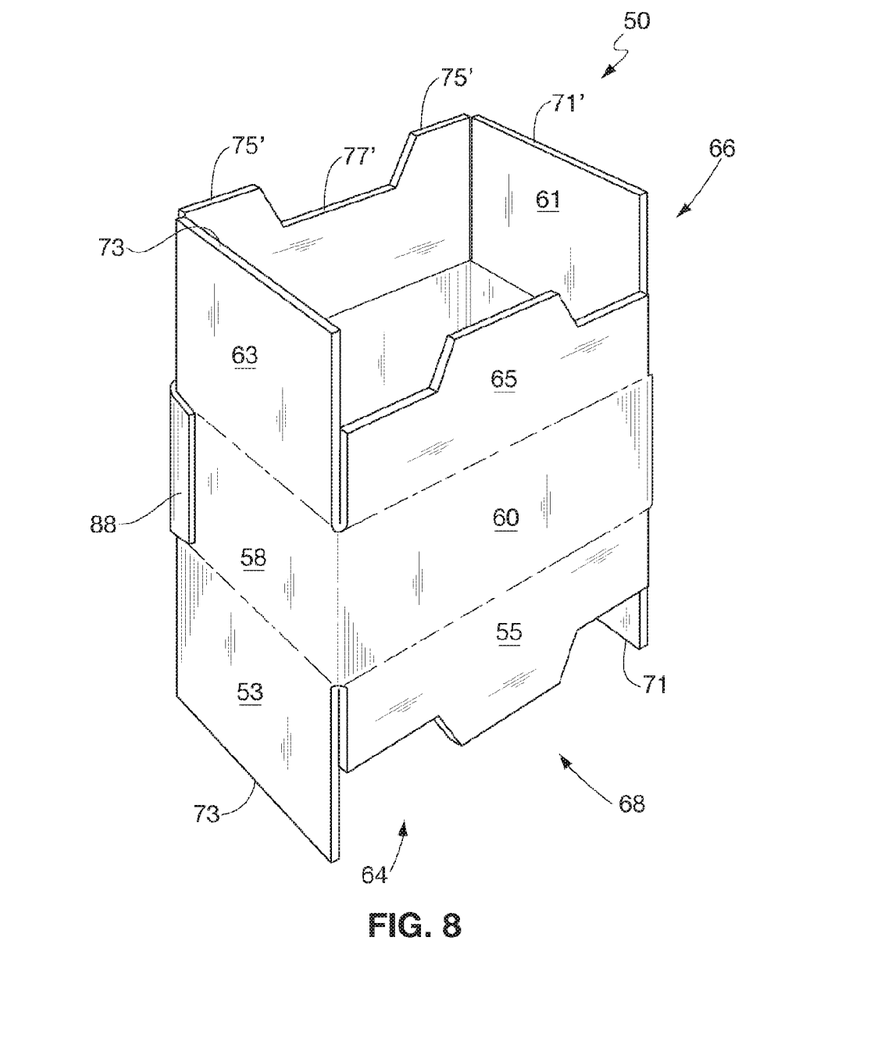
FIG. 8 is a perspective view of the carton wherein the first and second open ends of the carton interior are shown before the closure flaps are folded into the closed state.

As mentioned, product reservoir 30 described above also includes carton 50, which houses the flexible bag. As shown in FIGS. 6 and 8, carton 50 includes sidewall 52 shown in this exemplary embodiment to be constructed of four panels. Front panel 56 in opposed, parallel relationship to back panel 58 and a pair of oppositely disposed side panels 60 and 62 are spaced apart from one another and are parallel so as to extend between front and back panels 56 and 58. As shown here, the length of side panels 60 and 62 is greater than the length of front and back panels 56 and 58 such that carton 50 is generally rectangular in configuration. Sidewall 52 extends around carton interior 54, which is sized and adapted to receive and retain flexible bag 40 therein. For a flexible bag containing approximately 2.5 gallons of chemical treatment, carton 50 may have a length of approximately 13⅜", a width of approximately 9 5/16", and a depth of approximately 5⅛".

Carton interior 54 has opposite first and second open ends 64 and 66, which are provided with first and second end closures 68 and 70, respectively. With continued reference to FIGS. 6 and 8 and additional reference to FIG. 9, first end closure 68 is constructed of a plurality of first closure flaps, namely first front flap 51, first back flap 53, and a pair of first side flaps 55 and 57. Similarly, second end closure 70 is formed of a plurality of second closure flaps, namely second front flap 61, second back flap 63, and a pair of second side flaps 65 and 67. As may be appreciated, first and second end closures 68 and 70 are adapted to close the first and second openings 64 and 66, respectively, and enclose the carton interior to define a closed state.

As best shown in FIG. 6, carton 50 also includes spout opening 90, which communicates with carton interior 54 and is sized and adapted to permit at least a portion of spout 42 to extend therethrough, as shown in FIG. 5. Spout opening 90 is one continuous opening having a first portion 92 formed in first front flap 51 a second portion 94 formed in front panel 56. Second portion 94 is generally configured as a U-shaped opening that is sized and adapted to nestably receive the bag spout when extending therethrough. As will be discussed in more detail below, spout opening 90 is formed after removal of a perforated panel extending between both the front panel and first front flap.

Figure 10:
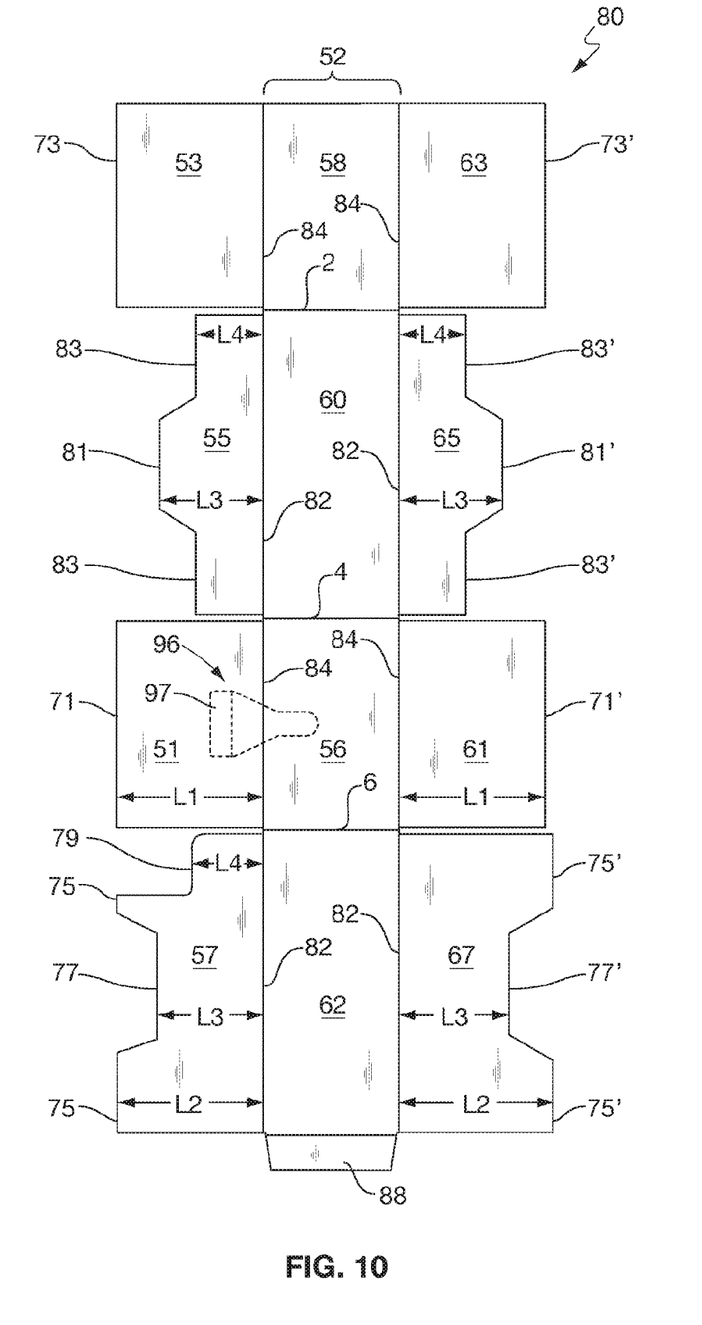
FIG. 10 is a top plan view showing a one-piece production blank used to construct the carton.

Turning to FIG. 10, the construction of carton 50 may be accomplished by means of a single, integral one-piece construction blank 80 constructed from corrugated fiberboard that is adapted to be folded and fastened into carton 50. The corrugated fiberboard may be single wall, double wall, or triple wall. With respect to a double wall corrugated construction, the construction may include five pieces of paperboard wherein the paperboard is specified in terms of boardweight as follows 42-26-42-26-42.

Sidewall 52 is formed by panels 56, 58, 60, and 62, which are foldable along longitudinally extending, parallel score lines 2, 4, and 6, which separate the panel pieces from one another, as well as score lines or transverse lines 82 and 84, which separate the panel pieces from closure flaps 51, 53, 55, 57, 61, 63, 65, and 67. As shown here, score lines 82 are longitudinally offset from score lines 84. This technique is known as "offset scoring" and is common in the art.

First and second front flaps 51, 61 are longitudinal extensions of front panel 56 while first and second back flaps 53, 63 are longitudinal extensions of back panel 58. Front and back closure flaps 51, 53, 61, and 63 extend longitudinally from score line 84 to terminate in an edge. Similarly, side flaps 55 and 65 are longitudinal extensions of side panel 60 while side flaps 57 and 67 are longitudinal extensions of side panel 62. Side closure flaps 55, 57, 65 and 67 each extend longitudinally from transverse fold line 82 to terminate in an edge. Longitudinal cuts 86 separate the closure flaps from each other.

Glue flap 88, which is formed as an extension of side panel 62 along score line 85, is adapted to adhere to and overlie back panel 58, as shown in FIG. 8, once sidewall 52 is formed. Glue flap 88 is shown as being adhered to the outer surface of panel 58, but could be adhered to the panel's inner surface. In addition, spout access panel 96 is defined by a series of perforations 99, which extend continuously between a portion of front panel 56 and first front flap 51 and is removable thereby to form the spout opening described above. Perforations 99 extend substantially through the thickness of the corrugated board so that it may be punched out in a conventional manner. Tab 97 may be provided to facilitate removal of panel 96. Tab 97 may be sized to be long enough to permit entry of the user's thumb or finger such that once it is forced out a sufficient distance, the user may grasp panel 96 and remove it.

As mentioned above, front, back, and side closure flaps 51, 53, 55, 57, 61, 63, 65, and 67 each terminate in an edge. First and second front flaps 51 and 61 each extends from score line 84 a length L1 to terminate in edges 71 and 71' respectively. Similarly, first and second back flaps 53 and 63 extend from score line 84 a length L1 to terminate at edges 73 and 73', respectively.

The first and second side flaps also terminate in respective edges, however, each flap includes edge portions that vary in length from the score line 82. First and second side flaps 57 and 67, which extend longitudinally from side panel 62, each has a portion thereof that extends a length L2 to terminate in edge portions 75 and 75' respectively. Due to the offset scoring, length L2 is less than length L1 such that edges 71 and 73, and edge portion 75 are longitudinally aligned with each other. Similarly, edges 71' and 73' and edge portion 75' are longitudinally aligned with one another. Additionally, each of first and second side flaps 57 and 67 includes a portion thereof that extends a length L3, which is less than L2, to terminate in edge portion 77 and 77', respectively. Additionally, first side panel 57 has a portion thereof that extends a length L4 to terminate in edge portion 79.

The remaining side flaps, 55 and 65, each extend longitudinally from side panel 60. Each flap 55, 65 has a portion that extends from score line 82 a length L5 to terminate in edge portion 81 and 81', respectively. Additionally, flaps 55 and 65 have a portion that extends a length L6 to terminate in edge portion 83 and 83', respectively.

The varying lengths of the closure flap edges facilitate the construction of carton 50 such that once constructed from production blank 80, some of the edge portions align in confronting relation to one another to provide strong first and second end closures for the carton interior. More particularly, during construction of carton 50, production blank 80 shown in FIG. 10 is first folded in half along score line 4. Glue flap 88 is then adhered to back panel 58. During this stage of the production process, carton 50 is in a flattened or collapsed configuration, known in the industry as a "knock down assembly."

After glue flap 88 is adhered to back panel 58, and before the adhesive is dry, the knock down assembly configuration of carton 50 is fed into a conventional squaring device. This squaring device includes two spaced apart, parallel plates that "knock", or otherwise come into contact with at least a portion of first and second closure flaps 51, 53, 57, 61, 63, and 67. This device is operative to "square up" the knock down assembly and adjust any misalignment of the glue flap. The plates of the squaring device will come into contact with the edges or edge portions that extend the length of either L1 or L2, namely, edges, 71, 71' 73, 73', 75 and 75'.

Figures 9, 11, 12:
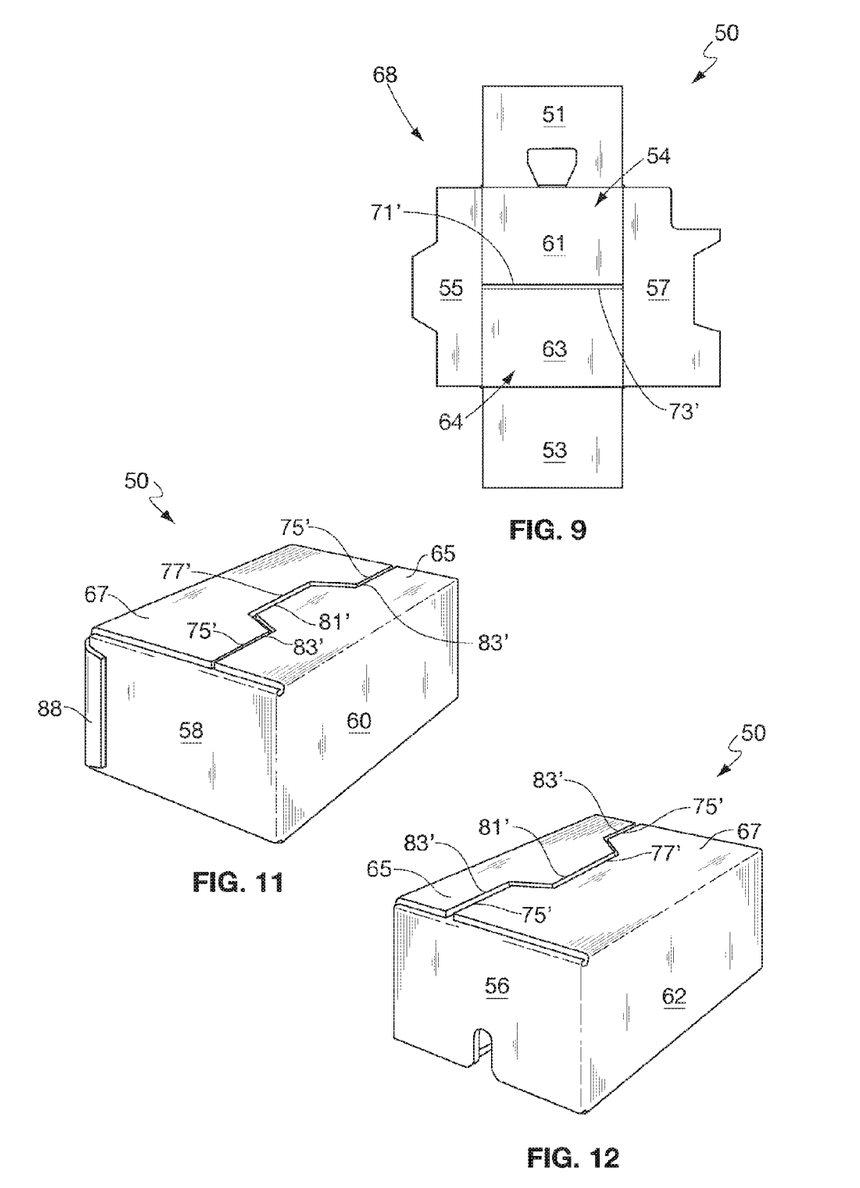
FIG. 9 is a top plan view of the carton showing the interior wherein the first closure flaps are folded outwardly, for perspective, and the second closure flaps are in the closed state.
FIG. 11 is a perspective view of the carton showing the glue flap overlying one of the panels of the carton.
FIG. 12 is a perspective view of the carton showing a portion of the spout opening formed in the front panel.

With reference to FIGS. 9-13, after being passed through the squaring device, the first and second end closures 68 and 70 can be folded inwardly to enclose the carton interior 54. To form the second closure end 70 second first and back flaps 61 and 63 are folded along transverse score lines 84 such that respective edges 71', 73' confront one another, such as shown in FIG. 9. Subsequently, flaps 65 and 67 are folded along transverse score lines 82 such that edge portions 81' and 83' of flap 65 confront edge portions 77' and 75' respectively, of flap 67, as best shown in FIGS. 11 and 12.

Figures 13, 14, 15, 16:
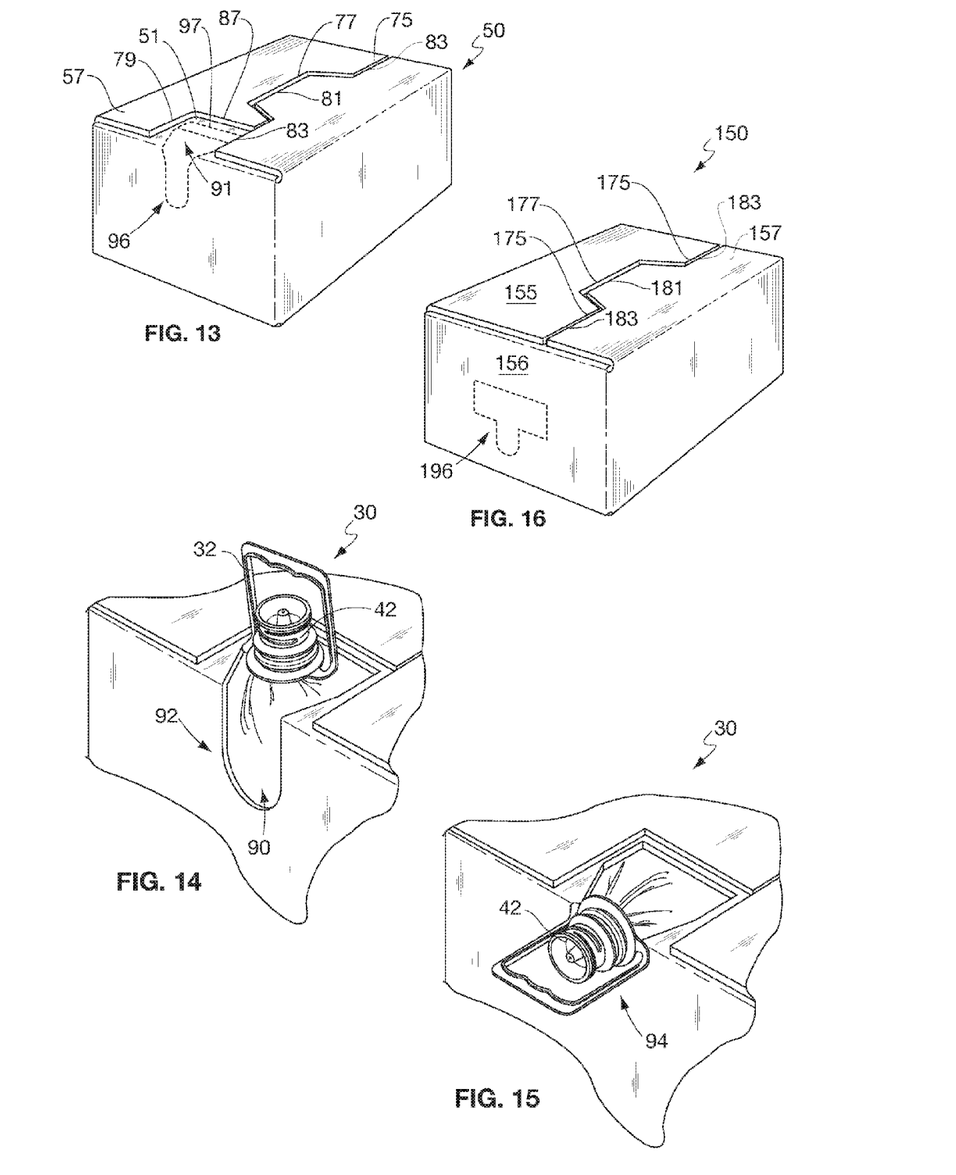
FIG. 13 is a perspective view of the carton showing the spout access panel before it has been removed.
FIG. 14 is a perspective view, partially cut-away, showing the spout extending through a first portion of the opening wherein the spout has a handled attached thereto to facilitate movement of the spout into position.
FIG. 15 is a perspective view, partially cut-away, showing the spout now nested in the U-shaped second portion of the opening in the front panel awaiting connection to the direct injection system.
FIG. 16 is a perspective view of a carton according to a second embodiment of the present invention, showing a spout access panel formed in the front panel prior to removal.

With continued reference to FIGS. 9-13, first end closure 68 is similarly formed whereby flaps 51 and 53 are folded along transverse score lines 84 such that their respective edges 71 and 73 are in confronting relationship with one another. Next, flaps 55 and 57 are folded along transverse score lines 82 whereby edge portions 75 and 77 of flap 57 confront edge portions 83 and 81, respectively, of flap 55. As shown, edge portion 79 of flap 57 is in spaced relation to edge portion 83 of flap 55, as best shown in FIG. 13. This space permits access to spout access panel 96. More particularly, as shown, edge portions 79 and 87 of flap 57, in combination with one of edge portions 83 of flap 55 surround that portion of spout access panel 96 that is associated with the first front flap 51. This facilitates access to panel 96 such that it can be removed, thereby to expose the opening and the spout associated with the flexible bag contained in the carton interior.

As may now be appreciated, once first and second end closures 68 and 70 are folded inwardly to enclose the carton interior, carton interior 54 is not accessible. If desired, the closure flaps may be retained in this closed state with a suitable adhesive, or other suitable method commonly known in the art. For illustration purposes, and with reference to FIGS. 9 and 13, first front and back flaps 51 and 53 may be folded inwardly over the second open end 66. Subsequently, first side flaps 55 and 57 are folded inwardly over top of flaps 51 and 53 and adhered thereto. As may also be appreciated, the configuration of first side flap 55 increase the surface area that may be adhered to both flaps 51 and 53. More particularly, the portion of first side flap 55 that extends beyond a length L6 increases the available surface area that can be used to adhere to flaps 51 and 53, while making efficient use of materials.

With the above described structure in mind, to construct the product reservoir disclosed herein, a flexible bag is filled with a selected liquid chemical product via the spout. The filled bag is placed in the carton interior and positioned such that the spout is positioned adjacent to or near the spout access panel. This placement allows for the spout to be accessible once the perforated access panel extending between the front panel and the first front flap is removed.

With reference to FIGS. 13-15, once the customer receives product reservoir 30, the perforated spout access panel 96 can be completely, or if desired, partially removed to form spout opening 90. Again, the removal of panel 96 may be facilitated by providing a punch tab 97 located adjacent to top portion 91. Once panel 96 is removed, spout 42 becomes accessible. If desired, the user can then attach handle 36 about spout 42, and pull spout out through opening 90, as shown in FIG. 13 to thereafter nest in spout in U-shaped second portion 94 thereof, as shown in FIG. 14. Handle 36 can have any suitable construction that would facilitate proper placement of spout 42. For example, handle 36 can have the features described in U.S. Pat. No. 6,394,517 B1, (the "'517 Patent") issued on May 28, 2002 to Borg and assigned to Oregon Precision Industries, located in Eugene, Oreg., the contents of which are incorporated herein by reference. Alternatively, the flexible bag can be provided with handle 36 at the time it is initially placed within the carton, allowing the user to simply grasp the handle once panel 96 is removed.

Once the spout is accessible, the customer can then place the entire product reservoir onto the farming equipment, for example in a bay, formed in the interior of a container such as described above with reference to FIG. 3. With the attachment of an appropriate coupler to the bag's spout, the product reservoir can then be interconnected with the direct injection system and used for treatment. As should be appreciated, the transfer of the chemical treatment is a closed transfer system. In other words, the customer does not need to come into direct contact with the liquid chemical treatment to prepare it for subsequent application. Rather, the customer simply needs to access the spout and couple the flexible bag to the direct injection system.

An alternative carton construction is shown in FIG. 16. Here, carton 150 is constructed similarly to carton 50 described above except that perforated spout access panel 196 is formed solely in front panel 156. Accordingly, opposing first side flaps 155 and 157 terminate in respective edges that are in confronting relation to one another when in the closed state. More specifically, edge portions 75 and 77 of flap 155 confront edge portions 81 and 83 when the flaps are in the closed state. Similar to the description above, once spout access panel 196 is removed, the spout associated with the flexible bag therein can be accessed and pulled through the opening so that the spout can be connected to the direct injection system.

Figure 17:
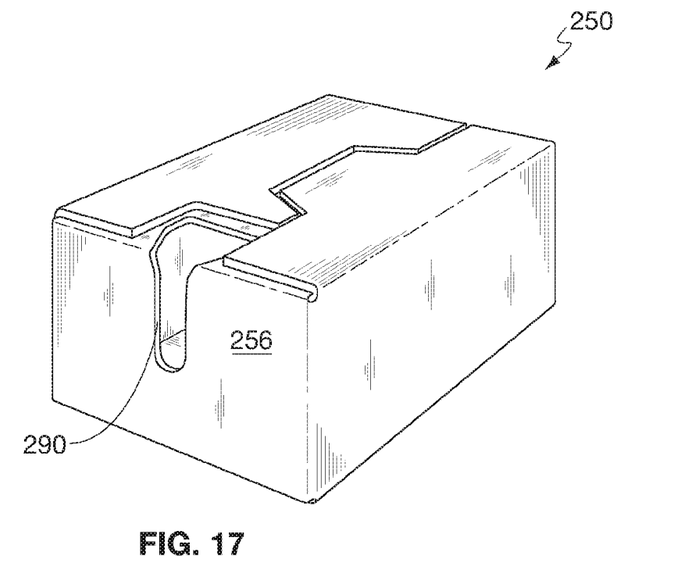
FIG. 17 is a perspective view of a carton according to a third embodiment of the present invention showing a spout opening formed in the front panel having an elongated U-shaped opening relative to the spout opening shown in FIG. 5.
Figure 18:
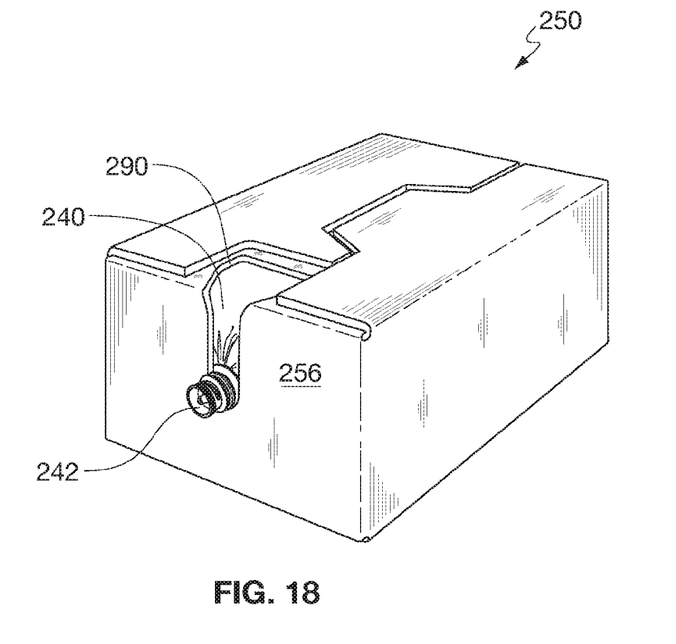
FIG. 18 is a perspective view of the carton shown in FIG. 17 with the bag enclosed therein and the spout extending through the spout opening.

FIGS. 17 and 18 show yet another carton construction. Here, spout opening 290 has the same general configuration as that shown for carton 50 in FIG. 5, for example. However, the U-shaped portion 294 of opening 290 is elongated such that it extends further down the length of front panel 256. In this way, once opening 290 is formed in the carton, spout 242 of bag 240 received therein may extend therethrough such that it is positioned further down the length of front panel 256. Locating spout 242 in this way may assist in the flow of the product out of bag 240 once connected to the direct injection system.

As shown in FIGS. 1 and 3, the product application system may be provided with a plurality of product reservoirs. As shown in the figures, product application system 10 includes two cabinets, each housing four product reservoirs for a total of eight product reservoirs. Accordingly, for illustration purposes, if each of the eight product reservoirs contains approximately 2.5 gallons of a concentrated selected chemical treatment, then the product application system is carrying approximately twenty gallons of the treatment. Depending upon the concentration of the product, the eight product reservoirs contain enough chemical product to treat approximately 100 acres. Further, it is contemplated that one or a plurality of conventional check valves could be associated with selected ones of the product reservoirs. The check valve would prevent the direct injection system from drawing the chemical treatment from the product reservoir. In this way, a customer could first exhaust the chemical treatment from a selected number of product reservoirs. Subsequently, if it is determined that additional chemical treatment is needed to treat the selected area, the stop valve could be removed or otherwise positioned to permit the treatment to be drawn therefrom by the direct injection system. Use of stop valves may help reduce the number of partially filled product reservoirs after treatment of the area has been completed.

Additionally, the product reservoir disclosed herein could include a plurality of flexible bags. For example, the carton interior could be sized and adapted to receive and retain two (2) separate flexible bags therein, each associated with a respective spout. The bags could be filled with the same liquid chemical treatment or different chemical treatments. The present disclosure also contemplates a method that is accomplished by the structures described above. Therefore, the method of the present invention relates to a method of applying a liquid chemical treatment, such as a pesticide to a selected area, such as an in-furrow application. The method includes providing a reservoir for the liquid chemical treatment as described above, connecting the reservoir to a system, such as a direct injection system, whereby the chemical treatment is drawn therefrom, and directing the chemical treatment to a delivery device operative to apply the treatment to the selected area. The chemical treatment may first be injected into a water stream and mixed in an inline chamber or other device prior to being dispensed through a delivery device such as a nozzle.

The method may also include the steps of first removing the access panel associated with the product reservoir, thereby to form or otherwise expose an opening that permit access to the flexible packaging in the carton. The method may also include the step of providing a plurality of product reservoirs and interconnecting each one of the reservoirs to the direct injection system.

From the foregoing, it should be appreciated that the product reservoir has a variety of uses beyond its association with the product application system shown in FIG. 1. For example, the product reservoirs herein described can be used for other agricultural application systems such as those associated with aircrafts.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

We claim:

1. A product reservoir adapted to contain a product to be dispensed to a selected area, comprising:
    a pesticide;
    a flexible bag having a bag interior adapted to receive and contain the pesticide, wherein the pesticide is positioned within said flexible baa, said bag including a spout in communication with the bag interior;
    a carton, including:
    (1) a sidewall extending around a carton interior that is sized and adapted to receive and retain said flexible bag and having first and second open ends opposite one another, said sidewall formed of a plurality of sidewall panels, including
        (a) a front panel and a back panel in parallel and spaced relation thereto; and
        (b) a pair of opposing side panels extending between said front and back panel;
    (2) a first closure formed by a plurality of first flaps operative to close the first open end when in a closed state, said first closure including:
        (a) a first front flap extending from said front panel and terminating in a first front flap edge;
        (b) a first back flap extending from said back panel and terminating in a first back flap edge wherein said first front and back flap edges confront one another when in the closed state;
        (c) a pair of first side flaps extending from a respective side panel and terminating in a respective first side flap edge wherein at least a majority of said first side flap edges confront one another when in the closed state;

(3) a second closure formed by a plurality of second flaps operative to close the second open end when in the closed state;

(4) a removable spout access panel having a first portion associated with said first front flap and a second portion associated with said front panel, wherein removal of said access panel exposes an opening formed therein and in communication with said carton interior, said opening sized to allow said spout to extend therethrough.

2. A product reservoir according to claim 1 wherein said side panels have a first length and said front and back panels have a second length, wherein said first length is greater than said second length.

3. A product reservoir according to claim 1 wherein said sidewall, said first and second closures, and said spout access panel are formed as an integral one-piece construction of corrugated fiberboard material.

4. A product reservoir according to claim 1 wherein a portion of each respective edge of said first side flaps are in spaced relation when in the closed state thereby to expose said spout access panel associated with said first front flap and the opening thereby formed after said access panel is removed.

5. A product reservoir according to claim 1 wherein said spout access panel is defined by a plurality of perforations extending substantially through said first front flap and said front panel and adapted to facilitate removal thereof.

6. A product reservoir according to claim 1 wherein the second portion of said spout access panel is generally U-shaped in configuration that is sized and adapted to nestably receive said spout.

7. A product reservoir according to claim 1 wherein said second closure includes:
(A) a second front flap extending from said front panel and terminating in a second front flap edge;
(B) a second back flap extending from said back panel and terminating in a second back flap edge wherein said second front and back flap edge confront one another when in the closed state;
(C) a pair of second side flaps extending from a respective side panel and terminating in a respective second side flap end wherein at least a majority of said second side flap ends a confront one another when in the closed state.

8. A product reservoir according to claim 1 wherein at least a portion of each of said first front flap, said first back flap, and one of said first side flaps has a common length measured from its respective panel piece to its respective flap edge.

9. A product reservoir according to claim 1 wherein said flexible bag includes a bag wall enclosing the bag interior formed of three flexible sheets.

10. A fluid delivery system adapted to dispense a liquid chemical product to a selected area for treatment, comprising:
a cabinet having at least one pair of stacked bins and a door configured to close and cover the at least one pair of stacked bins;
a flexible bag positioned within one of the stacked bins, wherein the flexible bag has a bag interior containing a pesticide, said bag including a spout communicating with the bag interior;
a delivery device in fluid communication with the bag interior and adapted to receive and dispense the chemical product to the selected area to be treated; and
a fluid pathway interconnecting said bag and said delivery device.

11. A fluid delivery system according to claim 10 including a carton having a carton interior sized and adapted to receive and retain said flexible bag.

12. A fluid delivery system according to claim 11 wherein said carton is formed of a corrugated material.

13. A fluid delivery system according to claim 10 including a water reservoir containing water therein, said water reservoir being in fluid communication with said delivery device.

14. A fluid delivery system according to claim 13 wherein the chemical product and the water are mixed prior to being dispensed through said delivery device.

15. A fluid delivery system according to claim 10 including a coupler adapted to interconnect the fluid pathway and said spout.

16. A fluid delivery system according to claim 10 including
(A) a plurality of flexible bags wherein each said bag contains a volume of the chemical product;
(B) a plurality of delivery devices; and
(C) an array of fluid pathways interconnecting said bags and said delivery devices.

17. A fluid delivery system according to claim 16 including a plurality of cartons each sized and adapted to receive and retain a respective one of said flexible bags.

18. A fluid delivery system according to claim 10 wherein the chemical product is an insecticide that is dispensed by said delivery device into a seed furrow.

19. A fluid delivery system according to claim 10 including a pump associated with the fluid pathway and operative to pump the chemical product from said bag to said delivery device.

20. A fluid delivery system according to claim 10 wherein said delivery device is a nozzle or a tube.

21. In an agricultural seed planting machine having a frame, a seed reservoir containing seeds supported by said frame, a plurality of row units mounted on said frame and operative to form a seed furrow and deposit the seeds into and the furrow at a selected rate, the improvement comprising:
(A) at least one cabinet defining a plurality of bins each for receiving at least one product reservoir, wherein said at least one cabinet is supported by said frame;
(B) a plurality of product reservoirs positioned within said at least one cabinet, wherein each said product reservoir includes:
(1) a flexible bag having a respective bag interior containing a chemical product to be dispensed in the seed furrow; and
(B) a carton, including a sidewall surrounding a carton interior sized and adapted to receive and retain said flexible bag;
(C) a direct injection system adapted to connect to said plurality of product reservoirs, including
(1) a plurality of fluid pathways interconnecting each one of said product reservoirs and the row units;
(2) a dispensing tube associated with each said row unit and operative to receive and dispense the chemical product to the furrow; and
(3) at least one pump operative to draw the chemical product from said flexible bag to said tube.

22. The improvement according to claim 21 including eight product reservoirs.

23. A closed transfer system for the application of agricultural chemicals to a selected area, comprising:
a cabinet having at least one pair of stacked bins and a door configured to close and cover the at least one pair of stacked bins;
a product reservoir positioned within one of the stacked bins, wherein the product reservoir includes (1) a carton having a sidewall surrounding a carton interior, said sidewall having an opening formed therethrough;

(2) a bag received in the carton interior having a bag interior containing an agricultural chemical and a spout communicating therewith, and wherein at least a portion of said spout extends through the opening in said carton sidewall;

a water reservoir containing water;

a first fluid pathway associated with said product reservoir and a second fluid pathway associated with said water reservoir;

a mixing chamber in fluid communication with said first and second fluid pathways wherein said water dilutes said agricultural chemical to form a mixture suitable for the application thereof; and a spray delivery device in fluid communication with said mixing chamber and operative to spray said application mixture to a selected area.

24. A closed transfer system according to claim 23 including at least one pump operative to draw the agricultural chemical and the water to the mixing chamber and transfer the mixture formed thereby to said spray delivery device.

25. A method of applying a liquid pesticide to a selected area from a delivery device, comprising the steps of:

(A) obtaining a pesticide reservoir, the reservoir including:

(1) a bag having an interior sized and adapted to contain the pesticide, wherein pesticide is positioned within the bag and a spout in communication with the pesticide; and (2) a carton adapted to receive said bag and pesticide contained therein, wherein the carton includes a spout access panel;

(B) opening the spout access panel and positioning the spout of the bag there through;

(C) securing the pesticide reservoir within the bin of a cabinet; and (D) directing said pesticide to the delivery device through which the pesticide is applied to the selected area.

26. A method according to claim 25 including a water reservoir containing water in fluid communication with said delivery device.

27. A method according to claim 26 including:

(A) drawing water from said water reservoir;

(B) mixing the water and said pesticide thereby to form a mixture at a location upstream from said delivery device; and (C) directing the mixture formed to said delivery device.

28. A method according to claim 27 including mounting said product reservoir on a planting assembly.

29. A method according to claim 28 including mounting a plurality of product reservoirs to said planting assembly.

30. A method according to claim 29 including mounting a water reservoir onto the planting assembly and connecting said water reservoir to the direct injection system.

31. A method of applying a liquid pesticide to a seed furrow formed by a planting assembly that is operative to form the seed furrow and deposit a seed therein and equipped with a direct injection system, said method comprising:

(A) positioning a product reservoir within a cabinet mounted on said planting assembly wherein said product reservoir includes:

(1) a bag having an interior sized and adapted to contain the pesticide; and (2) a carton adapted to receive said bag and pesticide contained therein;

(B) connecting said product reservoir to the direct injection system; and (C) directing the pesticide from said product reservoir to a nozzle associated with the direct injection system with sufficient force such that the liquid pesticide is sprayed into the seed furrow.

\* \* \* \* \*